US010005702B2

(12) United States Patent
Spannhoff et al.

(10) Patent No.: US 10,005,702 B2
(45) Date of Patent: Jun. 26, 2018

(54) CATALYST COATING AND PROCESS FOR THE CONVERSION OF OXYGENATES TO OLEFINS

(71) Applicant: BASF SE, Ludwigshafen (DE)

(72) Inventors: Kirsten Spannhoff, Mannheim (DE); Florina Corina Patcas, Ludwigshafen (DE); Ekkehard Schwab, Neustadt (DE); Alexander Weck, Freinsheim (DE); Kerem Bay, Ludwigshafen (DE); Matthias Mielke, Garbsen (DE); Oliver Seel, Nienburg (DE)

(73) Assignee: BASF SE, Ludwigshafen am Rhein (DE)

( * ) Notice: Subject to any disclaimer, the term of this patent is extended or adjusted under 35 U.S.C. 154(b) by 607 days.

(21) Appl. No.: 13/927,751

(22) Filed: Jun. 26, 2013

(65) Prior Publication Data
US 2014/0005456 A1  Jan. 2, 2014

Related U.S. Application Data

(60) Provisional application No. 61/665,920, filed on Jun. 29, 2012.

(51) Int. Cl.
B01J 29/06 (2006.01)
C07C 1/22 (2006.01)
B01J 29/40 (2006.01)
B01J 37/02 (2006.01)
C07C 1/20 (2006.01)
B01J 38/02 (2006.01)
B01J 23/02 (2006.01)
B01J 23/10 (2006.01)
B01J 29/70 (2006.01)
B01J 29/80 (2006.01)
B01J 29/90 (2006.01)
B01J 35/04 (2006.01)

(52) U.S. Cl.
CPC .............. C07C 1/22 (2013.01); B01J 23/02 (2013.01); B01J 23/10 (2013.01); B01J 29/061 (2013.01); B01J 29/40 (2013.01); B01J 29/70 (2013.01); B01J 29/7038 (2013.01); B01J 29/80 (2013.01); B01J 29/90 (2013.01); B01J 35/04 (2013.01); B01J 37/0215 (2013.01); B01J 37/0246 (2013.01); B01J 38/02 (2013.01); C07C 1/20 (2013.01); B01J 2029/062 (2013.01); C07C 2529/40 (2013.01); C07C 2529/70 (2013.01); C07C 2529/80 (2013.01); Y02P 20/584 (2015.11)

(58) Field of Classification Search
USPC ...................... 502/60, 77, 527.19
See application file for complete search history.

(56) References Cited

U.S. PATENT DOCUMENTS

| 4,049,573 | A |   | 9/1977  | Kaeding |
|-----------|---|---|---------|---------|
| 4,504,690 | A |   | 3/1985  | Forbus et al. |
| 4,548,914 | A |   | 10/1985 | Chu |
| 4,665,268 | A | * | 5/1987  | Lee ............. B01J 29/7034 585/640 |
| 4,692,423 | A |   | 9/1987  | Caesar |
| 4,800,187 | A | * | 1/1989  | Lachman .......... B01J 37/0246 502/60 |
| 5,164,350 | A | * | 11/1992 | Abe ................. B01D 53/945 502/66 |
| 6,417,421 | B1 | * | 7/2002 | Yao .................. B01J 29/40 585/418 |
| 6,770,251 | B2 | * | 8/2004 | Yoshikawa ....... B01D 53/8628 423/239.1 |
| 6,936,561 | B2 | * | 8/2005 | Marques .......... B01D 53/885 502/60 |
| 2002/0038775 | A1 |   | 4/2002  | Sterte et al. |
| 2009/0048093 | A1 |   | 2/2009  | Mizutani et al. |
| 2011/0142737 | A1 |   | 6/2011  | Seyler et al. |
| 2012/0116143 | A1 | * | 5/2012 | Okita ................ B01J 29/40 585/639 |
| 2014/0005455 | A1 |   | 1/2014  | Spannhoff et al. |
| 2014/0005457 | A1 |   | 1/2014  | Spannhoff et al. |
| 2014/0058180 | A1 |   | 2/2014  | Klingelhöfer et al. |

FOREIGN PATENT DOCUMENTS

| CN | 101239875 A  | 8/2008 |
| DE | 238733       | 9/1986 |
| DE | 238733 A1    | 9/1986 |
| EP | 2143700      | 1/2010 |
| EP | 2446964 A1   | 5/2012 |

(Continued)

OTHER PUBLICATIONS

Mitra et al., "Disporportionation of Toluene on ZSM5 Washcoated Monoliths", American Institute of Chemical Engineers, vol. 57, No. 12, 2011, pp. 3480-3495.*
Antia, J., et al., "Conversion of Methanol to Gasoline-Range Hydrocarbons in a ZSM-5 Coated Monolithic Reactior", Ind. Eng. Chem. Res., vol. 34, (1995) pp. 140-147.
Ciambelli, P., "Acid-Base Catalysis in the Conversion of Methanol to Olefins Over Mg-Modified Zsm-5 Zeolite", Successful Design of Catalysis, (1988), pp. 239-246.
Frieding, J., et al., "Extrusion of zeolites: Properties of catalysts with a novel aluminium phosphate sintermatrix", Applied Catalysis A: General, vol. 328, (2007), pp. 210-218.

(Continued)

Primary Examiner — Elizabeth D Wood
(74) Attorney, Agent, or Firm — Drinker Biddle & Reath LLP

(57) ABSTRACT

The present invention relates to a catalyst for the conversion of oxygenates to olefins, comprising
  a support substrate and
  a layer applied to the substrate,
wherein the layer comprises one or more zeolites of the MFI, MEL and/or MWW structure type, the one or more zeolites comprising one or more alkaline earth metals, to the preparation and use thereof, and to a process for converting oxygenates to olefins using the catalyst.

23 Claims, No Drawings

(56) References Cited

FOREIGN PATENT DOCUMENTS

| | | |
|---|---|---|
| JP | H7241471 A | 9/1995 |
| JP | H8243397 A | 9/1996 |
| JP | 2007/137840 | 6/2007 |
| JP | 20110121055 A | 6/2011 |
| RU | 2294799 C1 | 3/2007 |
| WO | WO-94/25151 A1 | 11/1994 |
| WO | WO-98/29519 A1 | 7/1998 |
| WO | WO-2009/092779 | 7/2009 |
| WO | WO-2011/089263 | 7/2011 |
| WO | WO-2012/123556 | 9/2012 |
| WO | WO-2012/123557 | 9/2012 |
| WO | WO-2012/123558 | 9/2012 |
| WO | WO-2013/017497 | 2/2013 |
| WO | WO-2014/001410 | 1/2014 |
| WO | WO-2014/001411 | 1/2014 |
| WO | WO-2014/001412 | 1/2014 |

OTHER PUBLICATIONS

Goryainova, T., et al., "Study of Magnesium-Containing Zeolite Catalysts for the Synthesis of Lower Olefins from Dimethyl Ether", Petroleum Chemistry, vol. 51, No. 3, (2011), pp. 169-173.

Hammon, U., et al., "Formation of Ethene and Propene from Methanol on Zeolite ZSM-5, II. Preparation of Finished Catalysts and Operation of a Fixed-Bed Pilot Plant", Applied Catalysis, vol. 37, (1998), pp. 155-174.

Ivanova S., et al., "ZSM-5 Coatings on β-SiC Monoliths: Possible New Structured Catalyst for the Methanol-to-Olefins Process", J. Phys. Chem. C, vol. 111, (2007), pp. 4368-4374.

Lee, Y., et al., "Novel aluminophosphate (AlPO) bound ZSM-5 extrudates with improved catalytic properties for methanol to propylene (MTP) reaction", Applied Catalysis A: General, vol. 374, (2010), pp. 18-25.

Lee, Y., et al., "Textural Properties and Catalytic Applications of ZSM-5 Monolith Foam for Methanol Conversion", Catal Lett, vol. 129, (2009), pp. 408-415.

McIntosh, R., et al., "The Properties of Magnesium and Zinc Oxide Treated ZSM-5 Catalysts for Conversion of Methanol Into Olefin-Rich Products", Applied Catalysis, vol. 6, (1983), pp. 307-314.

Okado, H., et al., "Deactivation Resistance of ZSM-5-Type Zeolites containing Alkaline Earth Metals used for Methanol Conversion", Applied Catalysis, vol. 41, (1988), pp. 121-135.

Patcas, F., et al., "The methanol-to-olefins conversion over zeolite-coated ceramic foams", Journal of Catalysis, vol. 231, (2005) pp. 194-200.

International Search Report for PCT/EP2013/063436, dated Jan. 7, 2014.

Yang, "Preparation of Modified ZSM-5/Cordierite Monolithic Catalyst and Their Catalytic Performance of Methanol to Olefin,"Dissertation (2011), Executive Summary.

Russian Office Action with Search Report for Russian Application No. 2015102718, dated May 25, 2017.

European Office Action for European Application No. 13 732 467.9, dated Sep. 27, 2017.

* cited by examiner

CATALYST COATING AND PROCESS FOR THE CONVERSION OF OXYGENATES TO OLEFINS

CROSS-REFERENCE TO RELATED APPLICATIONS

This application claims benefit (under 35 USC 119(e)) of U.S. Provisional Application 61/665,920, filed Jun. 29, 2012, which is incorporated by reference.

The present invention relates to a catalyst in the form of a coated support substrate for the conversion of oxygenates to olefins, and to a process for preparation thereof. The present invention further relates to a process for conversion of oxygenates to olefins, especially using the inventive coated support substrate as a catalyst, and to the use of a catalyst according to the present invention in specific catalytic processes.

INTRODUCTION

In view of increasing scarcity of mineral oil deposits which serve as starting material for preparation of lower hydrocarbons and derivatives thereof, alternative processes for preparing such commodity chemicals are becoming increasingly important. In alternative processes for obtaining lower hydrocarbons and derivatives thereof, specific catalysts are frequently used in order to obtain lower hydrocarbons and derivatives thereof, such as unsaturated lower hydrocarbons in particular, with maximum selectivity from other raw materials and/or chemicals. In this context, important processes include those in which methanol as a starting chemical is subjected to a catalytic conversion, which generally gives rise to a mixture of olefins, paraffins and aromatics.

In the case of such catalytic conversions, it is a particular challenge to refine the catalysts used therein, and also the process regime and parameters thereof, in such a way that a few very specific products form with maximum selectivity in the catalytic conversion. Thus, these processes are named particularly according to the products which are obtained in the main. In the past few decades, particular significance has been gained by those processes which enable the conversion of methanol to olefins and are accordingly characterized as methanol-to-olefin processes (MTO process for methanol to olefins). For this purpose, there has been development particularly of catalysts and processes which convert methanol via the dimethyl ether intermediate to mixtures whose main constituents are ethene and propene.

Antia et al. in Ind. Eng. Chem. Res. 1995, 34, pages 140-147 describes the coating of a support substrate with ZSM-5 and the use thereof in a methanol-to-gasoline process (MTG process).

U.S. Pat. No. 4,692,423 relates to a process for preparing a supported zeolitic catalyst by applying a mixture of a zeolite in a polymerizable solvent, for example tetrahydrofuran, to a porous support substrate, and the latter may consist of organic or inorganic material.

Ivanova et al. in J. Phys. Chem. C 2007, 111, pages 4368-4374 relates to a foamed molding and to an extrudate composed of β-silicon carbide, to each of which a ZSM-5 coating is applied, and to the use of such a coated foam body and extrudate in methanol-to-olefin processes (MTO processes). Compared to the use of the pulverulent zeolite per se, an improvement in the catalytic activity/selectivity is observed here, the coated catalysts having a higher stability with respect to deactivation by coking.

Patcas, F. C. in Journal of Catalysis 2005, 231, pages 194-200, describes ceramic foams coated with ZSM-5 zeolite and the use thereof in methanol-to-olefin processes. More particularly, it is stated that, in comparison to zeolitic pellets, such coated ceramic foams should exhibit an improvement in activity and selectivity. At relatively low temperatures and relatively high space velocities, however, lower space-time yields are described compared to the zeolitic pellets.

WO 98/29519 A1 describes nonzeolitic molecular sieves and especially SAPO supported on inorganic materials, and the use thereof in methanol-to-olefin processes.

WO 94/25151 A1 describes zeolites and especially ZSM-5 supported on monoliths, and the use thereof as a molecular sieve in separation processes.

Hammon et al. in Applied Catalysis 1988, 37, pages 155-174 relates to processes for producing zeolite extrudates with little to no binder and the use thereof in methanol-to-olefin processes. However, Hammon et al. describes the use of extrudates shaped to monoliths as catalysts as being particularly disadvantageous due to rapid coking and correspondingly short service lives.

Li et al. in Catal. Lett. 2009, 129, pages 408-415 relates to a foamed ZSM-5 monolith and to the use thereof in a methanol-to-olefin process.

DD 238733 A1 relates, for example, to a magnesium-doped zeolite and to the use thereof in the conversion of methanol to lower olefins, specifically of the carbon number range≥3. McIntosh et al. in Applied Catalysis 1983, 6, p. 307-314 describes specifically ZSM-5 catalysts and the use thereof in methanol-to-olefin processes, and the doping thereof with various metals and nonmetals, for example magnesium or phosphorus, and the influence thereof on the yields and product distribution in the catalytic conversion of methanol.

U.S. Pat. No. 4,049,573 relates to a catalytic process for conversion of lower alcohols and ethers thereof, and especially methanol and dimethyl ether, selectively to a hydrocarbon mixture with a high proportion of C2-C3 olefins and monocyclic aromatics and especially para-xylene, the catalysts used therein being doped with boron, magnesium and/or phosphorus.

Goryainova et al. in Petroleum Chemistry 2011, vol. 51, no. 3, p. 169-173 describes the catalytic conversion of dimethyl ether to lower olefins using magnesium-containing zeolites.

Ciambelli et al. "Acid-base catalysis in the conversion of methanol to olefins over Mg-modified ZSM-5 zeolite", Successful Design of Catalysts, Elsevier Science Publishers B.V., Amsterdam, 1988, p. 239-246 examines the influence of magnesium in the MTO process and especially in combination with ZSM-5 zeolite as a catalyst.

Okado et al. in Applied Catalysis 1988, 41, p. 121-135 relates to methanol-to-olefin processes using the ZSM-5 catalyst and examines the influence of various alkaline earth metals with regard to deactivation of the catalyst during the service life thereof.

Even though some advances have been achieved in the prior art with regard to the selectivities and/or activities of the catalysts by alterations to their composition and/or their configuration, especially also in methanol-to-olefin processes, there is still a considerable need for new catalysts and processes which, as well as new and/or improved selectivities, also have better resistance to any deactivation in such processes. This is especially true of those improvements which can lead to lower coking of the catalyst, in order thus to be able to enable a higher efficiency of existing and new processes.

DETAILED DESCRIPTION

It is thus an object of the present invention to provide an improved catalyst, especially for the conversion of oxygenates to olefins, which enables a longer service life of the catalyst with comparable space velocity and conversion of oxygenates. In this context, it was a particular object of the present invention to bring about improvements with regard to the coking of the catalyst which, for example in methanol-to-olefin processes, decides the service lives of a catalyst before regeneration of the catalyst is required, in order to achieve the desired selectivity and/or an adequate space-time yield.

It has been found that, surprisingly, a catalyst for the conversion of oxygenates to olefins, which comprises a support substrate and a layer applied to the substrate, the catalytically active layer comprising one or more zeolites of the MFI, MEL and/or MWW structure type, each of which comprise one or more alkaline earth metals, not only possesses a considerably improved service life but also a surprisingly high selectivity for $C_3$- and $C_4$-olefins. More particularly, it has also been found that, unexpectedly, the specific combination of the doping of one or more zeolites of the MFI, MEL and/or MWW structure type with one or more alkaline earth metals in combination with a configuration of the catalyst as a support substrate coated with the one or more zeolites results both in an unexpected improvement in the resistance of the catalyst to deactivation during the use thereof in a catalytic process and a surprisingly high olefin selectivity in the case of use of the catalyst for conversion of oxygenates.

The present invention thus relates to a catalyst for the conversion of oxygenates to olefins, comprising a support substrate and a layer applied to the substrate, wherein the layer comprises one or more zeolites of the MFI, MEL and/or MWW structure type, the one or more zeolites comprising one or more alkaline earth metals.

With regard to the support substrate used in the inventive catalyst, there is in principle no restriction whatsoever with regard to the form thereof. It is thus possible in principle to select any conceivable possible form for the support substrate, provided that it is suitable for being at least partially coated with a layer of the one or more zeolites of the MFI, MEL and/or MWW structure type. According to the present invention, however, it is preferred that the form of the support substrate is selected from the group consisting of granules, pellets, meshes, rings, spheres, cylinders, hollow cylinders and mixtures and/or combinations of two or more thereof. With regard to the preferred mixtures, these relate preferably to those forms of the support substrate which are commonly used for production of beds, this relating especially to the preferred forms of the support substrate selected from the group of the granules, pellets, meshes, rings, spheres, cylinders and hollow cylinders. On the other hand, with regard to the combinations of forms of the support substrate according to the present invention, preference is given to those combinations of beds and monoliths where the beds preferably comprise support substrates selected from the group consisting of granules, pellets, meshes, rings, spheres, cylinders, hollow cylinders and mixtures of two or more thereof. More particularly, such combinations of beds and monoliths relate to preferred forms of the catalyst in which a sequence of one or more monoliths and one or more beds is present, in which the bed(s) and monolith(s) form individual zones of the catalyst. Alternatively, however, preference is also given to embodiments of the inventive catalyst which comprise combinations of monoliths as the form of the support substrate, especially combinations of monoliths according to the particular or preferred embodiments as described in the present application. In particularly preferred embodiments of the present invention, the support substrate consists of one or more monoliths, and, in the case of use of a plurality of monoliths, a sequence and/or a succession of individual monoliths or plural monoliths arranged alongside one another at least in pairs is preferably present in the catalyst.

Thus, according to the present invention, preference is given to embodiments of the catalyst for the conversion of oxygenates to olefins in which the form of the support substrate is selected from the group consisting of granules, pellets, meshes, rings, spheres, cylinders, hollow cylinders, monoliths and mixtures and/or combinations of two or more thereof, the support substrate preferably being one or more monoliths.

With regard to the one or more monoliths which are preferably present as the support substrate in the inventive catalyst, there is again in principle no restriction with regard to the form that the one or more monoliths may take. According to the present invention, preference is given to monoliths selected from the group consisting of honeycombs, braids, foams and combinations of two or more thereof, and the one or more monoliths further preferably comprise one or more honeycombs and/or braids. More preferably, according to the present invention, the one or more monoliths which are preferably used as the support substrate are in honeycomb form.

Thus, according to the present invention, preference is further given to embodiments of the catalyst for the conversion of oxygenates to olefins in which the one or more monoliths as the preferred support substrate are selected from the group consisting of honeycombs, braids, foams and combinations of two or more thereof, the one or more monoliths preferably being in honeycomb form.

In the preferred embodiments which comprise one or more monoliths in honeycomb form, there are no particular restrictions whatsoever with regard to the honeycomb form, provided that it is suitable for being at least partially coated with the one or more zeolites of the MFI, MEL and/or MWW structure type. In particularly preferred embodiments, the honeycomb consists of a multitude of channels which run parallel to one another and which are divided from one another by the walls of the monolith, and the shape of the channels and/or preferably the thickness of the walls of the monolith which divide the channels from one another, up to a certain tolerance, are preferably the same both in terms of the shape of the channels and with regard to the wall thickness, the latter typically resulting from the material used for production of the monolith or the mode of production of the honeycomb or the honeycomb form. For example, preference is given to channels which have an angular shape, preferably the shape of a regular polyhedron having three or more vertices, preferably having three, four or six vertices and more preferably having four vertices. With regard to the dimensions of the channels in the preferred embodiments of the monoliths in honeycomb form, there is no restriction in principle, provided that the selected dimensions allow at least partial coating of the monolith in honeycomb form as the support substrate in the inventive catalyst with the one or more zeolites of the MFI, MEL and/or MWW structure type.

Thus, according to the present invention, it is possible to use, for example, monoliths in honeycomb form having 62 to 186 channels per square centimeter (400 to 1200 cpsi=cells per square inch), preference being given to monoliths in honeycomb form having 78 to 171 channels per square centimeter (500 to 1100 cpsi), further preference to those having 93 to 163 (600 to 1050 cpsi), further preference to those having 109 to 155 (700 to 1000 cpsi), further preference to those having 124 to 147 (800 to 950 cpsi) and further preference to those having 132 to 144 (850 to 930 cpsi). In particularly preferred embodiments of the present invention, according to which the support substrate comprises one or more monoliths in honeycomb form, those having 136 to 141 channels per square centimeter (880 to 910 cpsi) are used. In alternative embodiments of the present invention, and especially in preferred embodiments in which the layer applied to the substrate in the inventive catalyst further comprises a binder, monoliths with honeycomb are used having 8 to 124 channels per square centimeter (50 to 800 cpsi), preference being given to monoliths with honeycomb form having 23 to 109 channels per square centimeter (150 to 700 cpsi), further preferably those having 31 to 93 (200 to 600 cpsi), further preferably those having 39 to 85 (250 to 550 cpsi) and further preferably those having 47 to 78 (300 to 500 cpsi). In the alternative embodiments of the present invention, particular preference is given to embodiments in which the one or more monoliths with honeycomb form have 54 to 70 channels per square centimeter (350 to 450 cpsi).

In alternative embodiments of the present invention which use one or more monoliths as the support substrate in the catalyst, no substrate foams are present therein. Thus, preference is likewise given to embodiments of the catalyst in which the support substrate does not comprise any foams and more particularly does not comprise any foams as a monolith.

With regard to the substance of which the support substrate consists, and especially the beds and/or monoliths present therein, according to the present invention, there are no restrictions whatsoever in this regard, provided that it is suitable for being at least partially coated with the one or more zeolites of the MFI, MEL and/or MWW structure type. Thus, it is possible in principle to use any suitable material and/or any material composite as the substance for the support substrate, preference being given to using those materials which have high thermal stability and/or are inert to a high degree with regard to the chemical reactivity thereof. Thus, preference is given to using ceramic and/or metallic substances and composite materials of ceramic and/or metallic substances as the support substrate in the inventive catalyst, preference being given to using ceramic substances as the support substrate. With regard to the preferred ceramic substances, preference is given to using one or more of these substances selected from the group consisting of alumina, silica, silicates, aluminosilicates, silicon carbide, cordierite, mullite, zirconium, spinels, magnesia, titania and mixtures of two or more thereof. In a particularly preferred embodiment of the present invention, the ceramic substances preferably used for the support substrate are selected from the group consisting of α-alumina, silicon carbide, cordierite and mixtures of two or more thereof. In particularly preferred embodiments, the support substrate comprises cordierite, the support substrate further preferably being a cordierite substrate.

Thus, according to the present invention, preference is given to embodiments of the catalyst for the conversion of oxygenates to olefins in which the support substrate comprises ceramic and/or metallic substances, preferably ceramic substances, further preferably one or more substances selected from the group consisting of alumina, silica, silicates, aluminosilicates, silicon carbide, cordierite, mullite, zirconium, spinels, magnesia, titania and mixtures of two or more thereof, preferably from the group consisting of alpha-alumina, silicon carbide, cordierite and mixtures of two or more thereof, the support substrate more preferably being a cordierite substrate.

With regard to the one or more zeolites present in the catalyst, according to the present invention, there are no restrictions whatsoever either with regard to the type or with regard to the number of zeolites which can be used herein, provided that they are zeolites of one or more of the MFI, MEL and MWW structure types. If one or more of the zeolites present in the catalyst are of the MWW structure type, there is again no restriction whatsoever with regard to the type and/or number of MWW zeolites which can be used according to the present invention. Thus, these may be selected, for example, from the group of zeolites of the MWW structure type consisting of MCM-22, MCM-36, [Ga—Si—O]-MWW, [Ti—Si—O]-MWW, ERB-1, ITQ-1, PSH-3, SSZ-25 and mixtures of two or more thereof, preference being given to the use of zeolites of the MWW structure type which are suitable for the conversion of oxygenates to olefins, especially MCM-22 and/or MCM-36.

The same applies correspondingly to the zeolites of the MEL structure type which can be used according to the present invention in the catalyst, these being selected, for example, from the group consisting of ZSM-11, [Si—B—O]-MEL, boron-D (MFI/MEL mixed crystal), boralite D, SSZ-46, silicalite 2, TS-2 and mixtures of two or more thereof. Here too, preference is given to using those zeolites of the MEL structure type which are suitable for the conversion of oxygenates to olefins, especially [Si—B—O]-MEL.

According to the present invention, however, especially zeolites of the MFI structure type are used in the inventive catalyst for the conversion of oxygenates to olefins. With regard to these preferred embodiments of the present invention, there is likewise no restriction with regard to the type and/or number of the zeolites of this structure type used, the one or more zeolites of the MFI structure type which are used in the inventive catalyst preferably being selected from the group consisting of ZSM-5, ZBM-10, [Fe—Si—O]-MFI, [Ga—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof. Further preferably, according to the present invention, the catalyst comprises ZSM-5 and/or ZBM-10 as the zeolite of the MFI structure type, particular preference being given to using ZSM-5 as the zeolite. With regard to the zeolitic material ZBM-10 and the preparation thereof, reference is made, for example, to EP 0 007 081 A1 and to EP 0 034 727 A2, the content of which, particularly with regard to the preparation and characterization of the material, is hereby incorporated into the present invention.

Thus, according to the present invention, preference is given to embodiments of the catalyst for the conversion of oxygenates to olefins in which the one or more zeolites are of the MFI structure type, and are preferably selected from the group consisting of ZSM-5, ZBM-10, [As—Si—O]-MFI, [Fe—Si—O]-MFI, AMS-1B, AZ-1, boron-C, boralite C, encilite, FZ-1, LZ-105, monoclinic H-ZSM-5, mutinaite, NU-4, NU-5, silicalite, TS-1, TSZ, TSZ-III, TZ-01, USC-4, USI-108, ZBH, ZKQ-1B, ZMQ-TB and mixtures of two or more thereof, further preferably from the group consisting of ZSM-5, ZBM-10 and mixtures thereof, the zeolite of the MFI structure type preferably being ZSM-5.

In a preferred embodiment of the present invention, the catalyst does not comprise any significant amounts of one or more nonzeolitic materials and especially does not comprise any significant amounts of one or more aluminosilicophosphates (SAPOs). In the context of the present invention, the catalyst is essentially free of or does not comprise any significant amounts of a specific material in cases in which this specific material is present in the catalyst in an amount of 0.1% by weight or less based on 100% by weight of the total amount and the one or more zeolites of the MFI, MEL and/or MWW structure type, preferably in an amount of 0.05% by weight or less, further preferably of 0.001% by weight or less, further preferably of 0.0005% by weight or less and further preferably in an amount of 0.0001% by weight or less. A specific material in the context of the present invention particularly denotes a particular element or a particular combination of elements, a particular substance or a particular substance mixture, and also combinations and/or mixtures of two or more thereof.

The aluminosilicophosphates (SAPOs) in the context of the present invention include especially the SAPO materials SAPO-11, SAPO-47, SAPO-40, SAPO-43, SAPO-5, SAPO-31, SAPO-34, SAPO-37, SAPO-35, SAPO-42, SAPO-56, SAPO-18, SAPO-41, SAPO-39 and CFSAPO-1A.

According to the present invention, the one or more zeolites of the MFI, MEL and/or MWW structure type comprises one or more alkaline earth metals. In general, according to the present invention, there is no restriction whatsoever either with regard to the type and/or the number of alkaline earth metals present in the one or more zeolites, or with regard to the manner in which they are present in the one or more zeolites. Thus, the one or more zeolites may comprise one or more alkaline earth metals selected, for example, from the group consisting of magnesium, calcium, strontium, barium and combinations of two or more thereof. According to the present invention, the one or more alkaline earth metals, however, are preferably selected from the group consisting of magnesium, calcium, strontium and combinations of two or more thereof, and, in particularly preferred embodiments of the inventive catalyst, the alkaline earth metal is magnesium. In alternatively preferred embodiments of the present invention, the catalyst does not comprise any, or any significant amounts of, calcium and/or strontium.

Thus, according to the present invention, preference is given to embodiments of the catalyst for the conversion of oxygenates to olefins in which the alkaline earth metals present in the one or more zeolites of the MFI, MEL and/or MWW structure type are selected from the group consisting of Mg, Ca, Sr, Ba and combinations of two or more thereof, preferably consisting of Mg, Ca, Sr and combinations of two or more thereof, the alkaline earth metal more preferably being Mg.

With regard to the manner in which the one or more alkaline earth metals are present in the one or more zeolites in the catalyst, these may in principle be present in the micropores of the one or more zeolites and/or as a constituent of the zeolitic skeleton, especially at least partly in isomorphic substitution for an element in the zeolite skeleton, preferably for silicon and/or aluminum as a constituent of the zeolite skeleton and more preferably at least partly in isomorphic substitution for aluminum. With regard to the presence of the one or more alkaline earth metals in the micropores of the one or more zeolites, these may be present as a separate compound, for example as a salt and/or oxide therein, and/or as a positive counterion to the zeolite skeleton. According to the present invention, the one or more alkaline earth metals are present at least partly in the pores and preferably in the micropores of the one or more zeolites, and, further preferably, the one or more alkaline earth metals are present therein at least partly as the counterion of the zeolite skeleton, as can arise, for example, in the course of production of the one or more zeolites in the presence of the one or more alkaline earth metals and/or can be brought about by performance of an ion exchange with the one or more alkaline earth metals in the zeolite already produced.

With regard to the amount of the one or more alkaline earth metals, as already noted above, there are no particular restrictions according to the present invention with regard to the amount in which they are present in the one or more zeolites. It is thus possible in principle for any possible amount of the one or more alkaline earth metals to be present in the one or more zeolites, for example in a total amount of the one or more alkaline earth metals of 0.1-20% by weight based on the total amount of the one or more zeolites. According to the present invention, however, it is preferred that the one or more alkaline earth metals are present in a total amount in the range of 0.5-15% by weight based on 100% by weight of the total amount of the one or more zeolites, further preferably of 1-10% by weight, further preferably of 2-7% by weight, further preferably of 3-5% by weight and further preferably of 3.5-4.5% by weight. In particularly preferred embodiments of the present invention, the one or more alkaline earth metals are present in a total amount of 3.8-4.2% by weight in the one or more zeolites. For all of the above percentages by weight for alkaline earth metal in the one or more zeolites, these are calculated proceeding from the one or more alkaline earth metals as the metal.

Thus, according to the present invention, preference is given to embodiments of the catalyst for the conversion of oxygenates to olefins in which the one or more zeolites of the MFI, MEL and/or MWW structure type comprise the one or more alkaline earth metals in a total amount in the range from 0.1 to 20% by weight, preferably from 0.5 to 15% by weight, further preferably from 1 to 10% by weight, further preferably from 2 to 7% by weight, further preferably from 3 to 5% by weight, further preferably from 3.5 to 4.5% by weight, and further preferably in the range from 3.8 to 4.2% by weight, based in each case on the total amount of the one or more zeolites of the MFI, MEL and/or MWW structure type and calculated as the metal.

With regard to the components which may be present in the layer applied to the substrate in the inventive catalyst, there are no restrictions, provided that the catalyst is suitable for the conversion of at least one oxygenate to at least one olefin. Thus, in particular embodiments, the layer applied to the substrate may consist of the one or more zeolites of the MFI, MEL and/or MWW structure type comprising one or more alkaline earth metals. In further embodiments of the inventive catalyst, the layer applied to the substrate comprises one or more further components to the zeolites mentioned. With regard to the additional components to the one or more zeolites of the MFI, MEL and/or MWW structure type, there are no restrictions whatsoever, and so the layer applied to the substrate may comprise, for example, further catalytically active components, cocatalysts, fillers, support substances and/or binders, and combinations of two or more thereof. In preferred embodiments, the layer applied to the substrate further comprises a binder. In these preferred embodiments, any suitable binder may be present in the layer, and so one or more additional components which may be present in the layer applied act as binders and especially improve the coherence of the further components and especially of the one or more zeolites. Thus, for example, one or more components may be present in the layer as binders, selected from the group consisting of $SiO_2$, $Al_2O_3$, $TiO_2$, $ZrO_2$, MgO, clay minerals and mixtures of two or more thereof, the layer in a particularly preferred embodiment comprising $SiO_2$ as a binder in addition to the one or more zeolites of the MFI, MEL and/or MWW structure type.

With regard to the amount in which the one or more zeolites of the MFI, MEL and/or MWW structure type has been applied to the support substrate in the catalyst according to the present invention, there is in principle no restriction whatsoever, provided that a layer comprising the one or more zeolites can be formed at least partially on the support substrate. Thus, the inventive catalysts comprise, for example, the one or more zeolites of the MFI, MEL and/or MWW structure type in a total loading of 0.005-1 $g/cm^3$. According to the present invention, the term "loading" represents the amount of applied components of a layer in grams of dry substance per unit total volume of the support substrate. The volume relates here to the volume of the coated support substrate, and this in the case of bodies and forms comprising hollow bodies and/or recesses also comprises those cavities and recesses. In an alternative definition according to the present invention, the volume in the case of the loading of the support substrate, in embodiments comprising beds, is based on the respective volume of the bed including the intermediate spaces and cavities present therein. In preferred embodiments of the present invention, the catalyst comprises the one or more zeolites of the MFI, MEL and/or MWW structure type in a total loading of 0.01-0.5 $g/cm^3$ based on the volume of the coated support substrate and especially on the volume thereof according to the aforementioned particular and preferred definitions, further preferably in a total loading of 0.02-0.2 $g/cm^3$, further preferably of 0.04-0.1 $g/cm^3$, further preferably of 0.055-0.08 $g/cm^3$ and further preferably of 0.065-0.075 $g/cm^3$. In particularly preferred embodiments of the present invention, the catalyst comprises the one or more zeolites of the MFI, MEL and/or MWW structure type in a total loading of 0.07-0.072 $g/cm^3$ based on the volume of the coated support substrate according to the particular and preferred definitions of the present application.

Thus, according to the present invention, preference is given to embodiments of the catalyst for the conversion of oxygenates to olefins in which the catalyst comprises the one or more zeolites of the MFI, MEL and/or MWW structure type in a total loading of 0.005 to 1 $g/cm^3$ based on the volume of the coated support substrate, preferably in a total loading of 0.01 to 0.5 $g/cm^3$, further preferably of 0.02 to 0.2 $g/cm^3$, further preferably of 0.04 to 0.1 $g/cm^3$, further preferably of 0.055 to 0.08 $g/cm^3$, further preferably of 0.065 to 0.075 $g/cm^3$, and further preferably in a total loading of 0.07 to 0.072 $g/cm^3$.

In alternative embodiments of the present invention which are further preferred, and especially in preferred embodiments in which the layer applied to the substrate in the inventive catalyst further comprises a binder, the catalyst for the conversion of oxygenate to olefins comprises the one or more zeolites of the MFI, MEL and/or MWW structure type in a total loading of 0.01 to 0.8 $g/cm^3$ based on the volume of the coated support substrate, preferably in a total loading of 0.05 to 0.5 $g/cm^3$, further preferably of 0.08 to 0.3 $g/cm^3$, further preferably of 0.12 to 0.25 $g/cm^3$, further preferably of 0.15 to 0.23 $g/cm^3$, further preferably of 0.17 to 0.21 $g/cm^3$, and further preferably in a total loading of 0.18 to 0.2 $g/cm^3$.

The catalyst according to the present invention can be prepared in any suitable manner, provided that it comprises one or more zeolites of the MFI, MEL and/or MWW structure type which are present in a layer applied to a support substrate according to the present invention and especially according to one of the particular and preferred embodiments of the invention as described in the present application.

Thus, the present invention also relates to a process for preparing a catalyst according to the present invention, and especially according to one of the particular or preferred embodiments thereof, comprising (i) providing the support substrate and the one or more zeolites of the MFI, MEL and/or MWW structure type;
(ii) impregnating the one or more zeolites of the MFI, MEL and/or MWW structure type with a solution comprising the one or more alkaline earth metals, preferably by means of spray impregnation;
(iii) optionally drying the one or more impregnated zeolites obtained in (ii);
(iv) optionally calcining the one or more impregnated zeolites obtained in (ii) or (iii);
(v) preparing a mixture comprising the one or more impregnated and optionally dried and/or calcined zeolites of the MFI, MEL and/or MWW structure type and one or more solvents;
(vi) homogenizing the mixture obtained in (v);
(vii) coating the support substrate with the homogenized mixture obtained in (vi);
(viii) optionally drying the coated support substrate obtained in (vii);
(ix) optionally calcining the coated support substrate obtained in (vii) or (viii).

With regard to the manner of impregnation in step (ii) of the process according to the invention, the impregnation can be performed by any suitable process, for example an impregnation by soaking, spray impregnation and/or capillary impregnation. In particularly preferred embodiments of the process according to the invention, however, the impregnation in step (ii) is achieved by spray impregnation.

In the process according to the invention for preparing the inventive catalyst, especially in the particular and preferred embodiments described in the present application, there is in principle no restriction whatsoever with regard to the properties and especially the particle sizes and/or morphologies of the one or more zeolites of the MFI, MEL and/or MWW structure type provided in step (i). According to the particle size of the zeolites provided in step (i), however, one or more steps are optionally performed during the process according to the invention, preferably after the impregnation in step (ii) or after the preparation of the mixture in step (v), in order to bring the one or more zeolites to a preferred particle size. In this connection, there is at first no particular restriction with regard to the particle size of the one or more zeolites, provided that this is suitable for the performance of the further steps in the process according to the invention, especially according to the particular and preferred embodiments of the present invention, and the particle size should especially be suitable for performance of the coating in step (vii), more particularly depending on the nature and form of the support substrate used according to the present invention and especially according to the particular or preferred embodiments of the support substrate as described in the present application. Thus, in particular embodiments of the process according to the invention, one or more steps are performed after the impregnation in step (ii) or after the preparation of the mixture in step (v), preferably after the preparation of the mixture in step (v) and more preferably in step (vi) of the homogenizing of the mixture obtained in (v), in order to bring the one or more impregnated and optionally dried and/or calcined zeolites of the MFI, MEL and/or MWW structure type to a particle size $D_{50}$ in the range from 0.01 to 200 μm. In further preferred embodiments of the process according to the invention, the one or more zeolites, after one or more of the aforementioned steps, are brought in one or more steps to a particle size $D_{50}$ in the range from 0.03 to 150 μm, further preferably from 0.05 to 100 μm, further preferably from 0.1 to 50 μm, further preferably from 0.3 to 30 μm and even further preferably from 0.4 to 20 μm. In yet further preferred embodiments of the process according to the invention, the one or more impregnated and optionally dried and/or calcined zeolites, after the preparation of the mixtures in step (v) and preferably in step (vi) of the homogenizing of the mixture obtained in (v), is brought in one or more steps to a particle size $D_{50}$ in the range from 0.5 to 15 μm.

In further embodiments of the process according to the invention which are preferred, and especially in preferred embodiments in which a binder is used in the process according to the invention, one or more steps are performed after the impregnation in step (ii) or after the preparation of the mixture in step (v), preferably after the preparation of the mixture in step (v) and more preferably in step (vi) of the homogenizing of the mixture obtained in step (v), in order to bring the one or more impregnated and optionally dried and/or calcined zeolites of the MFI, MEL and/or MWW structure type to a particle size $D_{90}$ in the range from 0.5 to 50 μm. In further preferred embodiments of the process according to the invention, the one or more zeolites, after one or more of the aforementioned steps, are brought in one or more steps to a particle size $D_{90}$ in the range from 1 to 30 μm, further preferably from 3 to 20 μm, further preferably from 5 to 15 μm, and even further preferably from 9 to 11 μm. In yet further preferred embodiments of the process according to the invention, the one or more impregnated and optionally dried and/or calcined zeolites, after the preparation of the mixture in step (v) and preferably in step (vi) of the homogenizing of the mixture obtained in (v), is brought in one or more steps to a particle size $D_{90}$ in the range from 7 to 13 μm.

With regard to the number of steps and the manner in which the one or more zeolites are brought to a particular or preferred particle size $D_{50}$ and/or $D_{90}$, according to the present invention, there are no restrictions whatsoever, and so it is possible in principle to use any suitable process for this purpose. According to the present invention, the one or more zeolites, however, are preferably subjected to one or more grinding steps after one or more of steps (ii) and (v), and the one or more zeolites are more preferably brought to one of the particular or preferred particle sizes $D_{50}$ by the operation of homogenizing in step (vi), especially according to the particular and preferred embodiments of the present invention.

Thus, according to the present invention, preference is given to embodiments of the process for preparing a catalyst according to the present invention, and especially a catalyst according to one of the particular or preferred embodiments thereof, in which the impregnation in step (ii) or the preparation of the mixture in step (v), preferably the preparation of the mixture in step (v) and more preferably in step (vi) of the homogenizing of the mixture obtained in (v), is followed by bringing of the one or more impregnated zeolites of the MFI, MEL and/or MWW structure type to a particle size $D_{50}$ in the range from 0.01 to 200 μm, further preferably from 0.03 to 150 μm, further preferably from 0.05 to 100 μm, further preferably from 0.1 to 50 μm, further preferably from 0.3 to 30 μm, further preferably from 0.4 to 20 μm, even further preferably from 0.5 to 15 μm. Accordingly, preference is likewise given in accordance with the present invention to embodiments of the process for preparing a catalyst, and especially a catalyst according to one of the particular or preferred embodiments thereof, in which, after the impregnation in step (ii) or after the preparation of the mixture in step (v), preferably after the preparation of the mixture in step (v) and more preferably in step (vi) of the homogenizing of the mixture obtained in (v), the one or more impregnated zeolites of the MFI, MEL and/or MWW structure type is brought to a particle size $D_{90}$ in the range from 0.5 to 50 μm, further preferably from 1 to 30 μm, further preferably from 3 to 20 μm, further preferably from 5 to 15 μm, further preferably from 9 to 11 μm, and even further preferably from 7 to 13 μm.

According to the present invention, in the process according to the invention, a drying step is performed according to step (iii) and/or (viii). With regard to the manner in which the optional drying is achieved in one or more of these steps, there is no restriction in principle, and so the drying can be performed at any suitable temperature and in any suitable atmosphere. Thus, the optional drying can be effected under a protective gas atmosphere or in air, the optional drying preferably being effected in air. With regard to the temperature at which the drying is effected, it is possible, for example, to select a temperature in the range from 50 to 220° C. According to the present invention, the optional drying according to step (iii) and/or (viii) is effected at a temperature in the range from 70 to 180° C., further preferably from 80 to 150° C., further preferably from 90 to 130° C. and further preferably in the range from 100 to 125° C. In particularly preferred embodiments of the process according to the invention, the drying according to step (iii) and/or (viii) is effected at a temperature in the range from 110 to 120° C. With regard to the duration of the one or more optional drying steps, especially in particular and preferred embodiments of the process according to the invention, there is no particular restriction, provided that drying suitable for the further process steps can be achieved, for example after a drying step having a duration of 1 to 50 hours. In particular embodiments of the process according to the invention, the optional drying is performed for a period of 5 to 40 h, further preferably of 8 to 30 h, further preferably of 10 to 25 h, further preferably of 12 to 20 h and still further preferably of 14 to 18 h.

Thus, according to the present invention, preference is given to embodiments of the process for preparing a catalyst according to the present invention, and especially a catalyst according to one of the particular or preferred embodiments thereof, in which the drying in (iii) and/or (viii) is effected at a temperature in the range from 50 to 220° C., preferably from 70 to 180° C., further preferably from 80 to 150° C., further preferably from 90 to 130° C., further preferably from 100 to 125° C., and further preferably from 110 to 120° C.

With regard to the optional calcining steps according to the present invention, the same applies in principle as with regard to the optional drying steps, and so no particular restriction exists here either, either with regard to the temperature or with regard to the atmosphere in which the calcination is performed, and finally also not with regard to the duration of a calcination according to the particular and preferred embodiments of the present invention, provided that the product of the calcination is an intermediate suitable for being processed in the further steps of the process according to the invention to give a catalyst according to the present invention. Thus, for example, with regard to the temperature of the optional calcination in step (iv) and/or (ix), a temperature in the range from 300 to 850° C. may be selected, preference being given to selecting a temperature in the range from 350 to 750° C., further preferably from 400 to 700° C., further preferably from 450 to 650° C. and even further preferably from 480 to 600° C. In yet further preferred embodiments of the present invention, the calcination in the optional step (iv) and/or (ix) is performed at a temperature of 500 to 550° C. With regard to the atmosphere in which the optional calcination according to one or more of the aforementioned steps of the process according to the invention is performed, this may be either an inert atmosphere or air, the optional calcination in step (iv) and/or (ix) preferably being performed in air. Finally, there is also no restriction whatsoever with regard to the duration of the calcination step in the optional step (iv) and/or (ix), provided that the product of the calcination is suitable for further use, especially as an intermediate according to the optional step (iv), in the process according to the invention for preparing a catalyst, especially a catalyst according to one of the particular or preferred embodiments of the present application. Thus, the duration of the calcination according to one or more of the optional calcination steps in (iv) and/or (ix) may, for example, be 0.5 to 20 hours, preference being given to a duration of 1 to 15 h, further preferably of 2 to 10 h, further preferably of 3 to 7 h, and particular preference to a duration of 4 to 5 h.

Thus, according to the present invention, preference is given to embodiments of the process for preparing a catalyst according to the present invention, and especially a catalyst according to one of the particular or preferred embodiments thereof, in which the calcining in (iv) and/or (ix) is effected at a temperature in the range from 300 to 850° C., preferably from 350 to 750° C., further preferably from 400 to 700° C., further preferably from 450 to 650° C., further preferably from 480 to 600° C., and further preferably from 500 to 550° C.

In step (ii) of the process according to the invention, the one or more zeolites of the MFI, MEL and/or MWW structure type are first impregnated with a solution comprising one or more alkaline earth metals. According to the present invention, there is no restriction whatsoever in step (ii) with regard to the type and/or number of solvents used for this purpose. Thus, it is possible in principle to use any suitable solvent or solvent mixture in step (ii), provided that it is suitable for bringing about a corresponding impregnation of the materials defined therein, especially according to one of the particular and preferred embodiments of the present invention. This is equally true of the one or more solvents which are used in step (v) for preparation of the mixture defined therein, provided that the one or more solvents used for this purpose are suitable for enabling homogenization in step (vi) and the coating in step (vii). For example, it is possible in step (ii) and/or (v) to use one or more solvents selected from the group consisting of alcohols, water, mixtures of two or more alcohols and mixtures of water and one or more alcohols. In preferred embodiments of the present invention, the one or more solvents used in (ii) and/or (v) are selected from the group consisting of $(C_1-C_6)$-alcohols, water, mixtures of two or more $(C_1-C_6)$-alcohols and mixtures of water and one or more $(C_1-C_6)$-alcohols, the one or more solvents further preferably being selected from the group consisting of $(C_1-C_4)$-alcohols, water, mixtures of two or more $(C_1-C_4)$-alcohols and mixtures of water and one or more $(C_1-C_4)$-alcohols. In further preferred embodiments, the one or more solvents in steps (ii) and/or (v) are selected from the group consisting of methanol, ethanol, n-propanol, isopropanol, water and mixtures of two or more thereof, further preferably from the group consisting of methanol, ethanol, water and mixtures of two or more thereof, the solvent even further preferably being water, preferably distilled water.

Thus, according to the present invention, preference is given to embodiments of the process for preparing a catalyst according to the present invention, and especially a catalyst according to one of the particular or preferred embodiments thereof, in which the solution used in (ii) and/or the mixture prepared in (v) comprises one or more solvents selected from the group consisting of alcohols, water, mixtures of two or more alcohols, and mixtures of water and one or more alcohols, preferably from the group consisting of $(C_1-C_6)$ alcohols, water, mixtures of two or more $(C_1-C_6)$ alcohols, and mixtures of water and one or more $(C_1-C_6)$ alcohols, further preferably $(C_1-C_4)$ alcohols, water, mixtures of two or more $(C_1-C_4)$ alcohols, and mixtures of water and one or more $(C_1-C_4)$ alcohols, further preferably consisting of methanol, ethanol, n-propanol, isopropanol, water and mixtures of two or more thereof, further preferably consisting of methanol, ethanol, water and mixtures of two or more thereof, the solvent further preferably being water, preferably distilled water.

With regard to the solids concentration of the mixture provided in (v), according to the present invention, there are no particular restrictions whatsoever, provided that homogenizing of the mixture in step (vi) and the use of the homogenized mixture obtained in (vi) for the coating in (vii) are possible. Thus, the solids concentration of the mixture provided in (v) may, for example, be in the range of 5-50% by weight, the solids concentration according to the present invention preferably being in the range of 10-30% by weight and further preferably in the range of 15-25% by weight. In particularly preferred embodiments of the process according to the invention for preparing a catalyst, the solids concentration of the mixture provided in (v) is in the range of 18-22% by weight.

Thus, according to the present invention, preference is given to embodiments of the process for preparing a catalyst according to the present invention, and especially a catalyst according to one of the particular or preferred embodiments thereof, in which the solids concentration of the mixture prepared in (v) is in the range from 5 to 50% by weight, preferably from 10 to 30% by weight, further preferably from 15 to 25% by weight, and further preferably from 18 to 22% by weight.

In further embodiments which are preferred as an alternative, and especially in preferred embodiments in which a binder is used in the process according to the invention, the solids concentration of the mixture provided in (v) is in the range of 10-70% by weight, the solids concentration according to the present invention preferably being in the range of 20-50% by weight and further preferably in the range of 30-40% by weight. In particularly preferred embodiments of the process according to the invention for preparing a catalyst, the solids concentration of the mixture provided in (v) is in the range of 32-36% by weight.

With regard to the homogenizing in step (vi) too, according to the present invention, there is no particular restriction whatsoever, and so it is possible to select any conceivable procedure in order to obtain a homogeneous mixture of the mixture prepared in step (v), for which purpose it is possible to use, for example, one or more processes selected from the group consisting of stirring, kneading, agitating, vibration, or a combination of two or more thereof. According to the present invention, the mixture prepared in step (v) is preferably homogenized by stirring and/or by vibration in step (vi), the homogenization in step (vi) further preferably being effected by vibration, preferably by means of ultrasound, for example by use of an ultrasound bath into which the mixture to be homogenized is introduced.

Thus, according to the present invention, preference is given to embodiments of the process for preparing a catalyst according to the present invention, and especially a catalyst according to one of the particular or preferred embodiments thereof, in which the homogenizing in (vi) is effected by stirring, kneading, agitating, vibration or combinations of two or more thereof, preferably by stirring and/or vibration, further preferably by vibration, and further preferably by means of ultrasound.

With regard to the components which may be present in the mixture prepared in (v) and homogenized in (vi), there is no restriction whatsoever in principle, provided that a coated support substrate is obtained in (vi). Thus, in particular embodiments, the mixture prepared in (v) and/or homogenized in (vi) may consist of the one or more impregnated and optionally dried and/or calcined zeolites of the MFI, MEL and/or MWW structure type and one or more solvents. In further embodiments of the inventive catalyst, the mixture prepared in (v) and/or homogenized in (vi) comprises one or more further components to the zeolites and the solvent. With regard to the additional components which may be present in the mixture prepared in (v) and/or homogenized in (vi), there are no restrictions whatsoever in principle, and so the mixture in (v) and/or (vi) may comprise, for example, further catalytic components, cocatalysts, fillers, assistants, support substances, binders and combinations of two or more thereof. In particularly preferred embodiments, the mixture in (v) and/or in (vi) comprises a binder, in which case the binder may comprise one or more substances. In principle, the binder can be added to the mixture in (v), to the mixture in (vi), or both to the mixture in (v) and to the mixture in (vi), with addition in preferred embodiments of the binder to the mixture in (vi).

In the preferred embodiments in which the binder is added in (vi), this can in principle be added either before the homogenization of the mixture or at any time during the homogenization, provided that a homogenized mixture is obtained in (vi). In relation to preferred embodiments in which the one or more zeolites are brought in step (vi) to a particular $D_{50}$ and/or $D_{90}$ particle size, particular preference is given to embodiments in which one or more further components are added to the zeolites and the solvent, and especially to those in which an assistant is added, only after the establishment of the particle size.

With regard to the binder which is optionally added in the process, there are no restrictions, and so it is possible in principle to use any substance suitable for this purpose and any suitable mixture, provided that it leads to the desired increase in the coherence of the layer in the coated support substrate. Thus according to the present invention, for example, $SiO_2$, $Al_2O_3$, $TiO_2$, $ZrO_2$, MgO, clay minerals and mixtures of two or more thereof, and the respective precursor compounds thereof and mixtures of two or more thereof, and also mixtures of two or more of the former with two or more of the precursor compounds thereof can be used as binder in the inventive process.

$Al_2O_3$ binders and precursor compounds thereof which may be used are, for example, clay minerals and naturally occurring or synthetic aluminas such as alpha-, beta-, gamma-, delta-, eta-, kappa-, chi- or theta-alumina, and the inorganic and/or organometallic precursor compounds thereof, such as gibbsite, bayerite, boehmite, pseudoboehmite, or trialkoxyaluminates such as aluminum triisopropoxide.

Further binders which can be used in the process are montmorillonite, kaolin, bentonite, halloysite, dickite or nacrite.

Preferred binders comprise $SiO_2$ and/or one or more of the precursor compounds thereof, more preferably $SiO_2$, preference being given to using colloidal $SiO_2$. In embodiments which are further preferred, colloidal $SiO_2$ is added as a binder in (v) and/or (vi) and preferably in (vi).

With regard to the concentration of the binder in the homogenized mixture obtained in (vi), there are no restrictions, and so it is possible in principle to use any suitable amount of binder, provided that the resulting catalyst can be used for the conversion of at least one oxygenate to at least one olefin. Thus, the binder can be obtained, for example, in an amount of 0.1 to 50% by weight in (v) and/or (vi) and preferably in (vi), based on the total solids content of the homogenized mixture which is obtained in (vi). In further preferred embodiments, from 0.5 to 35% by weight of binder is added in (v) and/or (vi) and preferably in (vi), based on the total solids content of the homogenized mixture obtained in (vi), further preferably from 1 to 30% by weight, further preferably from 5 to 25% by weight, further preferably from 7 to 20% by weight, further preferably from 9 to 17% by weight, further preferably from 10 to 15% by weight, and still further preferably from 11 to 13% by weight.

With regard to the coating of the support substrate in step (vii) of the process according to the invention, there is in principle no restriction whatsoever with respect to the performance thereof, provided that a corresponding layer is formed at least partially on the support substrate. Thus, any suitable form of coating or of layer formation can be employed in the process according to the invention for preparing the inventive catalyst, the coating in step (vii) preferably being effected by spray coating and/or wash coating. In particularly preferred embodiments of the process according to the invention, the coating in step (vii) is effected by wash coating, the wash coating preferably being effected by dip coating. Such a preferred dip coating operation is effected, for example, by dipping the support substrate once or more than once into the mixture prepared in step (v) and homogenized in step (vi), and, according to the present invention, the dip coating is preferably followed by a treatment to remove excess mixture from the support substrate. In preferred embodiments of dip coating, in which the substrate is dipped repeatedly into the mixture prepared in step (v) and homogenized in step (vi), the further preferred treatment for removal of excess mixture can in principle be effected after the repeated dipping and/or between two or more dipping steps, each dipping step preferably being followed by removal of excess mixture by a suitable treatment of the coated support substrate. More preferably, however, according to the present invention, one dipping step into the mixture prepared in step (v) and homogenized in step (vi) is performed, followed by a corresponding treatment for removal of excess mixture.

With regard to the particularly preferred removal of excess mixture according to the particular embodiments of the present process, in which dip coating is performed in step (vii), there is in principle no restriction whatsoever with respect to the way in which excess mixture is removed. Thus, a removal can be achieved, for example, by suitable hanging of the coated support substrate and/or leaving it to stand, and/or directly or indirectly by mechanical or other action, for example by mechanical stripping and/or by removal with a suitable gas blower and/or by suitable application of centripetal forces, for example by means of centrifugal forces directed in a suitable manner. According to the present invention, however, particular preference is given to removing excess mixture by means of a gas blower, more preferably with the aid of compressed air by suitable extractive blowing of the excess mixture.

Thus, according to the present invention, preference is given to embodiments of the process for preparing a catalyst according to the present invention, and especially a catalyst according to one of the particular or preferred embodiments thereof, in which the coating in (vii) is effected by spray coating and/or wash coating, preferably by wash coating, the wash coating preferably being effected by dip coating, which is preferably followed by a treatment for removal of excess mixture, the removal of excess mixture preferably being effected at least partly with compressed air.

In the process according to the invention, according to the present invention, it is possible in principle to provide the support substrate with a plurality of layers of the same and/or different composition, especially with respect to the one or more zeolites of the MFI, MEL and/or MWW structure type. Thus, preference is given to embodiments of the process according to the invention for preparing a catalyst according to the present invention in which step (vii) is repeated once or more than once, step (viii) and/or step (ix) and preferably both step (viii) and step (ix) preferably being executed between the repetitions. In such preferred embodiments of the process according to the invention in which two or more layers of different composition, especially with respect to the one or more zeolites, are applied to the support substrate, steps (v) and (vi) are also repeated correspondingly in the case of preparation of the different compositions of the mixture in step (v), and this may relate not just to the chemical composition but also to the further properties of the mixture, for example the average particle size and/or the optional drying and/or the optional calcining of the one or more zeolites of the MFI, MEL and/or MWW structure type. If the differences in the mixtures prepared in step (v) for production of the different layers on the support substrate in these preferred embodiments also relate to the impregnation of the one or more zeolites of the MFI, MEL and/or MWW structure type in step (ii) of the process according to the invention and/or to optional drying and/or to optional calcining, and also to the manner of impregnation in step (ii) and/or of drying in step (iii) and/or of calcining in step (iv), steps (ii) and optionally (iii) and/or (iv) are also correspondingly repeated in these embodiments. In particularly preferred embodiments of the process according to the invention, steps (vii) and (viii) and/or (ix), preferably steps (vii)-(ix), are repeated once or more than once, in order to achieve multiple coating of the support substrate with a mixture prepared in step (v) and homogenized in step (vi).

With regard to the number of repetitions which are performed in the preferred embodiments of the process according to the invention for preparing a catalyst according to the present invention, there is no restriction in principle, and the steps in the repetitions of the particular and preferred embodiments of the process according to the invention are preferably repeated once to five times, further preferably once to four times, further preferably once to three times and further preferably once or twice.

Thus, according to the present invention, preference is given to embodiments of the process for preparing a catalyst according to the present invention, and especially a catalyst according to one of the particular or preferred embodiments thereof, in which step (vii) is repeated once or more than once, preferably steps (vii) and (viii), further preferably steps (vii) to (ix), and steps are preferably repeated once to five times, further preferably once to four times, further preferably once to three times, further preferably once or twice, and more preferably twice.

With regard to the temperature at which the coated support substrate obtained in (vii) is dried (viii), and to the duration of drying, there is no restriction in principle. For example, the optional drying in (viii) can be effected at a temperature in the range from 50 to 220° C., the drying preferably being effected at a temperature in the range from 80 to 200° C., further preferably in the range from 100 to 180° C., further preferably in the range from 110 to 170° C., further preferably in the range from 120 to 160° C., further preferably in the range from 130 to 150° C., and further preferably in the range from 135 to 145° C. With regard to the duration of drying, there is likewise no restriction whatsoever, and so it can be performed, for example, for a period of 0.1 to 5 h, the drying in step (viii) preferably being performed for a period of 0.2 to 2 h, further preferably of 0.3 to 1.5 h, further preferably of 0.4 to 1.2 h, further preferably of 0.5 to 1 h, further preferably of 0.6 to 0.9 h, and further preferably of 0.7 to 0.8 h.

With regard to the temperature at which the coated support substrate obtained in (vii) or (viii) is calcined in (ix), and to the duration of calcination, there is in principle no restriction whatsoever. For example, the optional calcination in (ix) can be effected at a temperature in the range from 250 to 1100° C., the calcination preferably being effected at a temperature in the range from 350 to 900° C., further preferably in the range from 400 to 800° C., further preferably in the range from 450 to 750° C., further preferably in the range from 500 to 700° C., further preferably in the range from 550 to 650° C., and further preferably in the range from 580 to 600° C. With regard to the duration of calcination, there is likewise no restriction whatsoever, and so this can be performed, for example, for a duration of 0.5 to 20 h, the calcination in step (ix) preferably being performed for a period of 0.75 to 15 h, further preferably of 1 to 10 h, further preferably of 1.5 to 5 h, further preferably of 2 to 4 h, further preferably of 2.5 to 3.5 h, and further preferably of 2.8 to 3.2 h.

In particularly preferred embodiments of the process according to the invention, the coated substrate obtained in (vii) is both dried and then calcined.

As well as a catalyst for the conversion of oxygenates to olefins according to the present invention as described in the present application, and especially according to the particular and preferred embodiments thereof, the present invention likewise relates to those catalysts for the conversion of oxygenates to olefins which are obtainable by the preparation process according to the invention, i.e. including catalysts per se which can be obtained by the preparation process according to the invention, without necessarily having to be prepared by this process. More particularly, the present invention thus relates to catalysts for the conversion of oxygenates to olefins which can be prepared by the process according to the invention, especially according to the particular and preferred embodiments thereof described in the present application, but can be or have been prepared by another process suitable for this purpose.

Thus, according to the present invention, preference is given to embodiments of the catalyst for the conversion of oxygenates to olefins in which the catalyst, and especially the catalyst according to one of the particular or preferred embodiments of the present invention, is obtainable by the process according to the invention for preparing a catalyst, preferably by one of the particular or preferred embodiments of the process according to the invention.

As well as a catalyst for the conversion of oxygenates to olefins and a process for preparing such a catalyst, the present invention also relates to a process for converting oxygenates to olefins. More particularly, the present invention relates to such a process comprising:

(1) providing a gas stream comprising one or more oxygenates;
(2) contacting the gas stream with a catalyst according to the present invention.

With regard to the catalyst which can be used in the process according to the invention for converting oxygenates to olefins, there is in principle no restriction whatsoever, provided that it is a catalyst according to the present invention as obtainable, for example, also by the process according to the invention, and provided that this catalyst is suitable for the conversion of at least one oxygenate to at least one olefin. This is especially true of the embodiments of the inventive catalyst according to the particular and preferred embodiments of the present invention.

The same applies correspondingly to the one or more oxygenate(s) present in the gas stream according to (1), and so there is no restriction here whatsoever in principle in the process according to the invention, provided that the one or more oxygenates present in the gas stream according to (1) can be converted by one of the catalysts according to the present invention and especially according to the particular and preferred embodiments thereof to at least one olefin when contacted according to (2). According to the present invention, however, it is preferable that the one or more oxygenates present in the gas stream according to (1) is selected from the group consisting of aliphatic alcohols, ethers, carbonyl compounds and mixtures of two or more thereof. Further preferably, the one or more oxygenates are selected from the group consisting of ($C_1$-$C_6$)-alcohols, di($C_1$-$C_3$)alkyl ethers, ($C_1$-$C_6$)-aldehydes, ($C_2$-$C_6$)-ketones and mixtures of two or more thereof, further preferably consisting of ($C_1$-$C_4$)-alcohols, di($C_1$-$C_2$)alkyl ethers, ($C_1$-$C_4$)-aldehydes, ($C_2$-$C_4$)-ketones and mixtures of two or more thereof. In yet further preferred embodiments of the present invention, the gas stream according to (1) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, the one or more oxygenates further preferably being selected from the group consisting of methanol, ethanol, dimethyl ether, diethyl ether, ethyl methyl ether and mixtures of two or more thereof. In particularly preferred embodiments of the process according to the invention for conversion of oxygenates to olefins, the gas stream according to (1) comprises methanol and/or dimethyl ether as the one or more oxygenates, and dimethyl ether is more preferably the oxygenate present in the gas stream according to (1).

Thus, according to the present invention, preference is given to embodiments of the process for converting oxygenates to olefins in which the gas stream according to (1) comprises one or more oxygenates selected from the group consisting of aliphatic alcohols, ethers, carbonyl compounds and mixtures of two or more thereof, preferably consisting of ($C_1$-$C_6$) alcohols, di($C_1$-$C_3$)alkyl ethers, ($C_1$-$C_6$) aldehydes, ($C_2$-$C_6$) ketones and mixtures of two or more thereof, further preferably consisting of ($C_1$-$C_4$) alcohols, di($C_1$-$C_2$) alkyl ethers, ($C_1$-$C_4$) aldehydes, ($C_2$-$C_4$) ketones and mixtures of two or more thereof, further preferably from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone and mixtures of two or more thereof, further preferably from the group consisting of methanol, ethanol, dimethyl ether, diethyl ether, ethyl methyl ether and mixtures of two or more thereof, the gas stream further preferably comprising methanol and/or dimethyl ether, and more preferably dimethyl ether.

On the other hand, with regard to the content of oxygenates in the gas stream according to (1) in the process according to the invention for converting oxygenates to olefins, there is no restriction according to the present invention here either, provided that, when the gas stream is contacted in (2) with a catalyst according to the present invention, at least one oxygenate can be converted to at least one olefin. In preferred embodiments, the content of oxygenates in the gas stream according to (1) is in the range from 30 to 100% by volume based on the total volume, the content especially being based on a gas stream at a temperature in the range from 200 to 700° C. and at a pressure of 101.3 kPa, preferably at a temperature in the range from 250 to 650° C., further preferably from of 300 to 600° C., further preferably from 350 to 560° C., further preferably from 400 to 540° C., further preferably from 430 to 520° C., and further preferably in the range from 450 to 500° C. and at a pressure of 101.3 kPa. According to the present invention, it is further preferred that the content of oxygenates in the gas stream according to (1) is in the range from 30 to 99% by volume, further preferably from 30 to 95% by volume, further preferably from 30 to 90% by volume, further preferably from 30 to 80% by volume, further preferably from 30 to 70% by volume, further preferably from 30 to 60% by volume and further preferably from 30 to 50% by volume. In particularly preferred embodiments of the process according to the invention for converting oxygenates to olefins, the content of oxygenates in the gas stream according to (1) is in the range from 30 to 45% by volume.

Thus, according to the present invention, preference is given to embodiments of the process for converting oxygenates to olefins in which the content of oxygenates in the gas stream according to (1) is in the range from 30 to 100% by volume based on the total volume, preferably from 30 to 99% by volume, further preferably from 30 to 95% by volume, further preferably from 30 to 90% by volume, further preferably from 30 to 80% by volume, further preferably from 30 to 70% by volume, further preferably from 30 to 60% by volume, further preferably from 30 to 50% by volume, and further preferably from 30 to 45% by volume.

With regard to the other components in the gas stream according to (1) in the process according to the invention, there is in principle no restriction whatsoever, provided that the gas stream is suitable overall for conversion of at least one of the oxygenates to at least one olefin in step (2) when contacted with a catalyst according to the present invention. In addition, for example, as well as the one or more oxygenates in the gas stream according to (1), one or more inert gases may also be present therein, for example one or more noble gases, nitrogen, water and mixtures of two or more thereof. In particular embodiments of the present invention, the gas stream according to (1) of the process according to the invention, as well as the one or more oxygenates, comprises water.

With regard to those preferred embodiments in which, as well as the one or more oxygenates, water is present in the gas stream according to (1), there is no restriction in principle with respect to the water content which may be present therein, provided that the conversion of at least one oxygenate in the gas stream to at least one olefin in step (2) of the contacting of the gas stream can be effected with a catalyst according to the present invention. In these preferred embodiments, however, it is preferable that the water content in the gas stream is in the range from 5 to 60% by volume based on the total volume, the water content more preferably being in the range from 10 to 55% by volume, further preferably from 20 to 50% by volume and further preferably from 30 to 45% by volume.

Thus, according to the present invention, preference is given to embodiments of the process for converting oxygenates to olefins in which water is present in the gas stream according to (1), preferably in the range from 5 to 60% by volume based on the total volume, preferably from 10 to 55% by volume, further preferably from 20 to 50% by volume, and further preferably from 30 to 45% by volume.

In particularly preferred embodiments of the process according to the invention for converting oxygenates to olefins, the gas stream provided in (1) originates from a preliminary reaction, preferably from the conversion of one or more alcohols to one or more ethers, especially from the conversion of one or more alcohols selected from the group consisting of methanol, ethanol, n-propanol, isopropanol and mixtures of two or more thereof, further preferably from the group consisting of methanol, ethanol, n-propanol and mixtures of two or more thereof, the gas stream provided in (1) more preferably originating from a preliminary reaction of methanol and/or ethanol and methanol further preferably being at least partly converted to one or more $di(C_1-C_2)$alkyl ethers, preferably to one or more $di(C_1-C_2)$alkyl ethers selected from the group consisting of dimethyl ether, diethyl ether, ethyl methyl ether and mixtures of two or more thereof. For instance, the gas stream provided in (1), in a particularly preferred embodiment, originates from a preliminary reaction of conversion of methanol to dimethyl ether.

In the particularly preferred embodiments of the process according to the invention in which the gas stream provided in (1) originates from a preliminary reaction of one or more alcohols, there is no particular restriction whatsoever in principle with respect to the reaction and hence the reaction product of the conversion of one or more alcohols, provided that this leads to a gas stream comprising one or more oxygenates which, when contacted in (2) with a catalyst according to the present invention, enables the conversion of at least one of the oxygenates to at least one olefin. In these particular embodiments, it is further preferable that the preliminary reaction leads to conversion of at least one alcohol to at least one ether and especially to at least one dialkyl ether, the preliminary reaction more preferably being a dehydration in which water is obtained as a coproduct to one or more dialkyl ethers. In the particular and preferred embodiments of the present invention in which the gas stream provided in (1) originates from a preliminary reaction, it is particularly preferred in the process according to the invention that such a gas stream originating from a preliminary reaction is supplied directly and without workup to the process according to the invention in step (1).

With respect to the manner of contacting the gas stream with a catalyst according to the present invention in step (2) of the process according to the invention for converting oxygenates to olefins, there is in principle no restriction whatsoever, provided that the conversion of at least one oxygenate to at least one olefin can be implemented. This applies, for example, to the temperature at which the contacting (2) takes place. Thus, for example, the contacting in step (2) of the process according to the invention can take place at a temperature in the range from 200 to 700° C., preference being given to selecting temperatures in the range from 250 to 650° C., further preferably from 300 to 600° C., further preferably from 350 to 560° C., further preferably from 400 to 540° C. and further preferably from 430 to 520° C. In particularly preferred embodiments of the present invention, the contacting according to (2) of the process according to the invention is performed at a temperature in the range from 450 to 500° C.

Thus, according to the present invention, preference is given to embodiments of the process for converting oxygenates to olefins in which the contacting according to (2) is effected at a temperature in the range from 200 to 700° C., preferably from 250 to 650° C., further preferably from 300 to 600° C., further preferably from 350 to 560° C., further preferably from 400 to 540° C., further preferably from 430 to 520° C., and further preferably from 450 to 500° C.

The same applies correspondingly to the pressure at which the gas stream is contacted in step (2) of the process according to the invention with the catalyst according to the present invention. Thus, the contacting can in principle take place at any desired pressure, provided that this allows the conversion of at least one oxygenate to at least one olefin by virtue of the contacting of the gas stream with the catalyst. Thus, the pressure, for example in the contacting in step (2), may be in the range from 0.1 to 10 bar, the pressure according to the present application indicating the absolute pressure, such that a pressure of 1 bar in the contacting accordingly corresponds to the standard pressure of 1.03 kPa. According to the present invention, the contacting in step (2) takes place preferably at a pressure from 0.3 to 7 bar, further preferably from 0.5 to 5 bar, further preferably from 0.7 to 3 bar, further preferably from 0.8 to 2.5 bar and further preferably from 0.9 to 2.2 bar. In particularly preferred embodiments of the process according to the invention for converting oxygenates to olefins, the contacting in step (2) takes place at a pressure of 1 to 2 bar.

Thus, according to the present invention, preference is given to embodiments of the process for converting oxygenates to olefins in which the contacting according to (2) is effected at a pressure in the range from 0.1 to 10 bar, preferably from 0.3 to 7 bar, further preferably from 0.5 to 5 bar, further preferably from 0.7 to 3 bar, further preferably from 0.8 to 2.5 bar, further preferably from 0.9 to 2.2 bar, and further preferably from 1 to 2 bar.

In addition, there are no particular restrictions with respect to the manner of performance of the process according to the invention for converting oxygenates to olefins, and so it is possible to use either a continuous or a noncontinuous process, the noncontinuous process being performable, for example, in the form of a batch process. According to the present invention, it is preferable to conduct the process according to the invention for the conversion of oxygenates as a continuous process. Thus, according to the present invention, preference is given to embodiments of the process for converting oxygenates to olefins in which the process is a continuous process.

With respect to these preferred embodiments of a continuous process, there are no restrictions whatsoever with respect to the space velocity selected, provided that the conversion of an oxygenate to an olefin can be effected. Thus, it is possible to select, for example, space velocities in the contacting in step (2) which are in the range from 0.5 to 50 $h^{-1}$, preference being given to selecting space velocities (WHSV=weight hourly space velocity is calculated as the ratio of oxygenate reactant stream in kg/h to the amount of zeolite in the reactor in kg) from 1 to 30 $h^{-1}$, further preferably from 3 to 25 $h^{-1}$, further preferably from 5 to 20 $h^{-1}$, further preferably from 7 to 15 $h^{-1}$ and further preferably from 8 to 12 $h^{-1}$. In particularly preferred embodiments of the process according to the invention for converting oxygenates, space velocities for the contacting of the gas stream in step (2) in the range from 9 to 11 $h^{-1}$ are selected. In alternative embodiments of the continuous process, and especially in preferred embodiments in which the layer applied to the substrate in the catalyst further comprises a binder, space velocities in the course of contacting in step (2) in the range from 0.1 to 20 $h^{-1}$ may be selected, preference being given to selecting space velocities of 0.5 to 15 $h^{-1}$, further preferably of 1 to 10 $h^{-1}$, further preferably of 1.5 to 8 $h^{-1}$, further preferably of 2 to 7 $h^{-1}$, further preferably of 2.5 to 6 $h^{-1}$, further preferably of 3 to 5 $h^{-1}$, and further preferably of 3.5 to 4.5 $h^{-1}$.

Thus, according to the present invention, preference is given to embodiments of the process for converting oxygenates to olefins in which the space velocity in the course of contacting according to (2) is in the range from 0.5 to 50 $h^{-1}$, preferably from 1 to 30 $h^{-1}$, further preferably from 3 to 25 $h^{-1}$, further preferably from 5 to 20 $h^{-1}$, further preferably from 7 to 15 $h^{-1}$, further preferably from 8 to 12 $h^{-1}$, and further preferably from 9 to 11 $h^{-1}$. Accordingly, preference is likewise given in accordance with the present invention to embodiments of the process for converting oxygenates to olefins in which the space velocity in the course of contacting in step (2) is in the range from 0.1 to 20 $h^{-1}$, preferably from 0.5 to 15 $h^{-1}$, further preferably from 1 to 10 $h^{-1}$, further preferably from 1.5 to 8 $h^{-1}$, further preferably from 2 to 7 $h^{-1}$, further preferably from 2.5 to 6 $h^{-1}$, further preferably from 3 to 5 $h^{-1}$, and further preferably from 3.5 to 4.5 $h^{-1}$.

As described above and shown in the examples of the present application, it is possible to achieve particularly long service lives with the inventive catalyst in a process for converting oxygenates as described in the present application, especially with respect to the particular and preferred embodiments of the process according to the invention. It has thus been found that, surprisingly, the use of a catalyst according to the present invention can considerably increase the service life of the catalyst before the process has to be interrupted for regeneration of the catalyst, at least with respect to the use of this catalyst batch compared to the use of catalysts according to the prior art. It is thus particularly preferable according to the present invention to select long service lives for the performance of the process for converting oxygenates to olefins at one of the particular or preferred space velocities, as described in the present application.

Thus, preference is given to service lives in the range from 15 to 400 h, further preferably in the range of 20 to 300 h, further preferably from 60 to 250 h, further preferably from 90 to 220 h, further preferably from 110 to 200 h, further preferably from 130 to 180 h, further preferably from 150 to 170 h and further preferably from 155 to 165 h. More particularly, based on the particular and preferred space velocities at which the process according to the invention is performed, preference is thus given, for example, to service lives of 15 to 400 h at a space velocity in the range from 0.5 to 50 $h^{-1}$. Further preference is given to a service life of 20 to 300 h at a space velocity of 1 to 30 $h^{-1}$, further preference to a service life of 60 to 250 h at a space velocity of 1 to 30 $h^{-1}$, further preference to a service life of 90 to 220 h at a space velocity of 3 to 25 $h^{-1}$, further preference to a service life of 110 to 200 h at a space velocity in the range from 5 to 20 $h^{-1}$, further preference to a service life of 130 to 180 h at a space velocity in the range from 7 to 5 $h^{-1}$ and further preferably of 150 to 170 h at a space velocity of 8 to 12 $h^{-1}$. In a particularly preferred embodiment of the process according to the invention, a service life of the catalyst, during which the continuous process is performed without interruption, in the range from 155 to 165 h at a space velocity of 9 to 11 $h^{-1}$ is selected.

In alternative embodiments of the present invention, and especially in preferred embodiments in which the layer applied to the substrate in the catalyst further comprises a binder, preference is given to service lives in the range from 5 to 800 h, further preferably in the range from 10 to 600 h, further preferably in the range from 30 to 550 h, further preferably in the range from 50 to 500 h, further preferably in the range from 70 to 450 h, further preferably in the range from 80 to 420 h, further preferably in the range from 90 to 400 h, and further preferably in the range from 100 to 380 h. More particularly, based on the particular and preferred space velocities at which the process according to the invention is performed in alternative embodiments, and especially in preferred embodiments in which the layer applied to the substrate in the catalyst further comprises a binder, preference is thus given, for example, to service lives of 5 to 800 h at a space velocity in the range from 0.1 to 20 $h^{-1}$. Further preference is given to a service life of 10 to 600 h at a space velocity of 0.5 to 15 $h^{-1}$, further preference to a service life of 30 to 550 h at a space velocity of 1 to 10 $h^{-1}$, further preference to a service life of 50 to 500 h at a space velocity of 1.5 to 8 $h^{-1}$, further preference to a service life of 70 to 450 h at a space velocity of 2 to 7 $h^{-1}$, further preference to a service life of 80 to 420 h at a space velocity of 2.5 to 6 $h^{-1}$, further preference to a service life of 90 to 400 h at a space velocity of 3 to 5 $h^{-1}$, and further preference to a service life of 100 to 380 h at a space velocity of 3.5 to 4.5 $h^{-1}$.

According to the present invention, the particular and preferred embodiments with respect to the service life selected and especially the service lives selected in combination with particular space velocities preferably relate to a minimum conversion of the one or more oxygenates present in the gas stream according to (1) of the process according to the invention, sustained conversion below this value leading to subsequent performance of the regeneration of the catalyst. According to the present invention, there is no particular restriction with respect to the minimum conversion selected, this preferably allowing full conversion of the one or more oxygenates present in the gas stream according to (1) of the process according to the invention during the service life of the catalyst. Thus, in preferred embodiments of the present invention, a minimum conversion of 60% of the one or more oxygenates present in the gas stream according to (1) of the process according to the invention is selected, sustained conversion below this value leading to performance of the regeneration of the catalyst, preferably a minimum conversion of 70% or more, further preferably of 80% or more, further preferably of 85% or more, further preferably of 90% or more, further preferably of 95% or more, further preferably of 97% or more, further preferably of 98% or more, and further preferably of 99% or more of the one or more oxygenates present in the gas stream according to (1) of the process according to the invention.

Thus, according to the present invention, further preference is given to embodiments of the process for converting oxygenates to olefins in which the service life of the coated support substrate as a catalyst, during which the continuous process is performed without interruption, is in the range from 15 to 400 h, preferably from 20 to 300 h, further preferably from 60 to 250 h, further preferably from 90 to 220 h, further preferably from 110 to 200 h, further preferably from 130 to 180 h, further preferably from 150 to 170 h, and still further preferably from 155 to 165 h.

The present invention further also relates to the use of the inventive catalyst as described above, and especially to the use of the inventive catalyst according to the particular and preferred embodiments as described in the present application. According to the present invention, there is no restriction whatsoever in principle with respect to the use of the inventive catalyst, and so it can be used either for the conversion of oxygenates to olefins or in any conceivable catalytic process in which the catalyst exhibits a corresponding catalytic action with respect to a chemical conversion. According to the present invention, however, the inventive catalyst is preferably used in a methanol-to-olefin process (MTO process), and further preferably in a methanol-to-gasoline process (MTG process), in a methanol-to-hydrocarbon process, in a methanol-to-propylene process (MTP process), in a methanol-to-propylene/butylene process (MT3/4 process) and for alkylation of aromatics, or in a fluid catalytic cracking process (FCC process). According to the present invention, however, the inventive catalyst is preferably used in a methanol-to-olefin process (MTO process), more preferably in a methanol-to-propylene/butylene process (MT3/4 process), especially in a process for converting oxygenates to olefins in one of the particular or preferred processes for converting oxygenates to olefins according to the present invention.

EXAMPLES

Comparative Example 1: Preparation of an Extrudate Comprising H-ZSM-5

380 g of H-ZSM-5 (ZEO-cat PZ2-100 H from Zeochem) with Si/Al=50 were mixed with 329 g of pseudoboehmite (Pural SB; Sasol), 10 g of formic acid in 50 ml of water were added, and the mixture was processed with 300 ml of water in a kneader to give a homogeneous material. The starting weights were selected such that the zeolite/binder ratio in the calcined extrudates corresponds to 60:40. This kneaded material was pushed with the aid of an extrudate press at approx. 100 bar through a 2.5 mm die. The extrudates were subsequently dried in a drying cabinet at 120° C. for 16 h and (after heating time 4 h) calcined in a muffle furnace at 500° C. for 4 h. Thereafter, the extrudates were processed in a sieving machine with 2 steel balls (diameter approx. 2 cm, 258 g/ball) to give 1.6-2.0 mm spall.

Comparative Example 2: Preparation of a Support Coated with H-ZSM-5 (Loading: 71 g/l)

An aqueous suspension having a solids concentration of 40% by weight of H-ZSM-5 zeolite (ZEO-cat PZ2-100 H from Zeochem) with Si/Al=50 was prepared and homogenized in an ultrasound bath. Cylindrical honeycomb pieces of cordierite (900 cpsi, diameter 0.9 cm, length=11 cm) were dipped into this suspension and then blown dry with compressed air. The coated supports were then dried at 110° C. for 1 h and subsequently calcined at 550° C. for 3 h. The coating step was repeated until a loading of 0.5 g of zeolite per honeycomb piece (0.071 g/cm$^3$) was attained, the amount of suspension applied being reported in grams of dry substance per liter of total honeycomb volume.

Example 1

Preparation of a Support Coated with Mg-ZSM-5 (Loading: 71 g/l)

H-ZSM-5 (ZEO-cat PZ2-100 H from Zeochem) with Si/Al=50 powder was spray impregnated with an amount of magnesium nitrate solution corresponding to 90% of its water uptake capacity. The amount of Mg weighed in was such that the powder after the calcination comprises 4% by weight of Mg. For impregnation, 58.7 g of zeolite powder were introduced into a round-bottom flask and placed in a rotary evaporator. 43.9 g of magnesium nitrate were dissolved in water while heating, and made up to 54 ml of total liquid with dist. water. The resulting magnesium nitrate solution was introduced into a dropping funnel, and sprayed gradually onto the powder through a glass spray nozzle flooded with 100 l/h of $N_2$ while rotating. At regular intervals during this time, the flask was detached and shaken by hand, in order to achieve homogeneous distribution. On completion of addition of the magnesium nitrate solution, the powder was rotated further for 10 min. Subsequently, the powder was dried at 120° C. in a quartz rotary sphere flask for 16 h, then calcined at 500° C. under air (20 l/h) for 5 h, and the calcined powder was subsequently ground to a small size with the aid of an analytical mill and sieved through a sieve having a mesh size of 1 mm.

The BET surface area of the resulting magnesium-impregnated zeolite was 303 m$^2$/g.

Elemental analysis:
Mg: 4 g/100 g

The Mg-ZSM-5 powder prepared by spray impregnation was applied to honeycomb pieces according to comparative example 2, with a solids concentration of Mg-ZSM-5 in the aqueous suspension used for this purpose of 20% by weight. The coating step was repeated according to comparative example 2 until a loading of 0.5 g of Mg-ZSM-5 per honeycomb piece (0.071 g/cm$^3$) was attained.

Example 2: Preparation of a Support Coated with Mg-ZSM-5 (Loading: ~85 g/l)

Distilled water was initially charged in a vessel with a propeller stirrer. While continuously stirring and adjusting the speed, Mg-ZSM-5 powder which was prepared according to example 1 was added gradually until a solids content of 33% by weight had been attained. This was followed by grinding of the Mg-ZSM-5 starting suspension in a stirrer ball mill to a particle size $D_{90}$ of 10 μm. During the grinding, the temperature did not exceed 30° C. After the grinding, Ludox AS-40 was added as a binder. The solids content of the binder was 12% by weight overall, based on the total solids content of the final suspension.

To prepare the support substrate, the suspension was applied to a honeycomb (cordierite honeycomb having a cell density of 400 cpsi (62 cells/cm$^2$) and a wall thickness of 6-7 mil (152.4 μm-177.8 μm)). For this purpose, the suspension was diluted to a solids content of 28%. The catalyst was immersed into the suspension over the full height, such that all cells were completely filled. After a wait time of 10 seconds, the substrate was extracted from the suspension, turned over and freed of excess suspension with compressed air from the inlet to the outlet side.

Subsequently, the catalyst was dried in a dryer by means of hot air (140° C.), alternately from both sides with a respective cycle time of 10 seconds, for a total of 45 minutes. Thereafter, the catalyst was calcined in a flow calciner at a maximum temperature of 590° C., and the catalyst during the operation passed through three heating zones, one constant temperature zone and one cooling zone within three hours.

The loading of the carrier substrate was calculated by means of a mass balance to be 0.085 g/cm$^3$.

Example 3: Preparation of a Support Coated with Mg-ZSM-5 (Loading: ~150 g/l)

The preparation method according to example 2 was repeated, except the support substrate was coated twice. For this purpose, the suspension was first diluted to a solids content of 26% with distilled water, and the catalyst was coated therewith according to example 2, and the layer was then thermally fixed. The suspension was then diluted further to a solids content of 25%, and the operation of coating and thermal fixing according to example 2 was repeated with this suspension, achieving a loading of the support substrate of 0.15 g/cm$^3$.

Example 4: Preparation of a Support Coated with Mg-ZSM-5 (Loading: ~190 g/l)

The preparation method according to example 2 was repeated, except the support substrate was coated repeatedly as in example 3. For this purpose, the suspension was first diluted to a solids content of 28% with distilled water, and the catalyst was coated therewith according to example 2, and the layer was then thermally fixed. The suspension was then diluted further to a solids content of 25%, and the operation of coating and thermal fixing according to example 2 was repeated with this suspension, achieving a loading of the support substrate of 0.19 g/cm$^3$.

Example 5: Comparative Tests in the Methanol-to-Propylene/Butylene Process (MT3/4 Process)

2 g of the catalyst prepared according to comparative example 1 were mixed with 24 g of silicon carbide and installed in a continuous, electrically heated tubular reactor, such that the bed in the reactor has a length of 30 cm and a diameter of 12 mm. For the tests using the catalysts prepared according to comparative example 2 and according to examples 1 to 4, two of the coated honeycomb bodies in each case were installed in the reactor and sealed at the tube wall with glass fiber cord.

Upstream of the test reactor, methanol vapor was produced to give a gas stream comprising 75% by volume of methanol and 25% by volume of N$_2$, which was converted to dimethyl ether by means of a preliminary reactor charged with 34 ml of alumina spall at 275° C. and an (absolute) pressure of 1-2 bar. The stream comprising dimethyl ether was then passed into the tubular reactor, and converted therein at a temperature of 450 to 500° C., a WHSV (=weight hourly space velocity), according to the specimen, in the range from 3.6 to 10 h$^{-1}$ based on methanol and an (absolute) pressure of 1 to 2 bar, and the reaction parameters were maintained over the entire run time. Downstream of the tubular reactor, the gaseous product mixture was analyzed by on-line chromatography.

The results achieved in the MT3/4 process for the catalysts according to comparative examples 1 and 2 and according to examples 1 to 4 with respect to the selectivities are shown in table 1, these reproducing the average selectivities during the run time of the catalyst in which the conversion of methanol was 95% or more.

TABLE 1

Average selectivities of a cycle (methanol conversion of >95%).

| | Comparative example 1 | Comparative example 2 | Example 1 | Example 2 | Example 3 | Example 4 |
|---|---|---|---|---|---|---|
| Loading [g/l] | — | 71 | 71 | 82 | 156 | 192 |
| Service life [h] | 33 | 53 | 160 | 99 | 271 | 381 |
| WHSV [h$^{-1}$] | 10 | 7 | 10 | 8.4 | 4.4 | 3.6 |
| MeOH load per cycle [kg$_{MeOH}$ · kg$_{zeolite}^{-1}$] | 330 | 371 | 1600 | 832 | 1192 | 1372 |
| Selectivity [%]: | | | | | | |
| ethylene | 9 | 8 | 6 | 5.3 | 8.1 | 10.7 |
| propylene | 24 | 19 | 32 | 44.2 | 39.4 | 39.8 |
| butylene | 15 | 17 | 27 | 27.1 | 29.2 | 28.2 |
| C$_4$ paraffins | 10 | 12 | 4 | 1.7 | 2.3 | 2.2 |
| C$_{5+}$ (mixture) | 16 | 18 | 25 | 15.3 | 13.4 | 10.2 |
| aromatics | 19 | 18 | 5 | 4.3 | 5.2 | 6.0 |
| C$_1$-C$_3$ paraffins | 7 | 8 | 2 | 2.2 | 2.4 | 2.8 |

As can be inferred from the values in table 1, surprisingly, the specific use of an alkaline earth metal-comprising zeolite which has been applied to a support substrate in an MT3/4 process leads not only to very high selectivities with respect to propylene and butylene in the product stream, but these are also maintained over a surprisingly long period, as can be seen from the unexpectedly high service lives of the catalyst for which a conversion of methanol of more than 95% can be maintained.

As can be seen from the results for comparative examples 1 and 2 and for example 1 in table 1, it has been found that an increase in the service life or an unexpected increase in the MeOH load per cycle which is achieved by the application of the zeolite to a substrate can unexpectedly be increased by several times through the additional use of an alkaline earth metal zeolite. All the more surprising, however, is the fact that this simultaneously brings about an unexpected and particularly also constant selectivity of the catalyst according to example 1 extending as far as the $C_3$ and $C_4$ olefins propylene and butylene. Thus, the present invention provides a catalyst for the conversion of oxygenates to olefins which, as has been shown by the test results in the MT3/4 process according to example 5, has an unexpectedly high selectivity with respect to $C_3$ and $C_4$ olefins, which is associated with surprisingly long service lives, especially compared to a catalyst which is present in extrudate form (see comparative example 1) or which has been applied to a support substrate but does not comprise any alkaline earth metal (see comparative example 2).

As can be seen from the results for the catalysts from examples 2, 3 and 4, which comprise a binder compared to example 1, the considerable improvement in service life was observed in spite of the use of a binder. More particularly, a constantly higher loading of the catalyst in examples 3 and 4 achieved a further considerable rise in the service life, even though it was not quite possible to attain the methanol load per cycle which is observed in example 1. On the other hand, however, the use of a binder leads to a catalyst having a much higher durability through the better adhesion of the layer.

Very surprisingly, however, it was found that the use of a binder leads to a further rise in the selectivity of the catalyst for the $C_3$- and $C_4$-olefins. More particularly, a considerable jump is observed in the selectivity for the $C_3$-olefins in example 2 compared to example 1, which already shows a considerable rise compared to the selectivities for $C_3$- and $C_4$-olefins in the comparative examples. This occurs particularly without trade-offs with regard to the selectivities for $C_4$-olefins, which corresponds to the results of example 1. In the case of each increase in the loading in examples 3 and 4, a likewise very high selectivity for $C_3$-olefins is observed compared to example 1, and especially to the comparative examples. Surprisingly, however, the selectivity for $C_4$-olefins increases in examples 3 and 4, the highest selectivity being observed for example 3.

Thus, the present invention also provides a catalyst for the conversion of oxygenates to olefins which, through the use of a binder, not only increases the durability of the catalyst but also the service life thereof through the possibility of using higher loadings of the catalyst on the support substrate. More particularly, however, it has been found that, surprisingly, the specific use of a binder in the inventive catalyst was able to result in to a further improvement in the selectivity for $C_4$-olefins, and more particularly also for $C_3$-olefins. Accordingly, the present invention provides a greatly improved catalyst for the conversion of oxygenates to olefins, which especially has long services lives combined with simultaneously high selectivities for $C_3$- and $C_4$-olefins.

PRIOR ART DOCUMENTS CITED

Antia et al. in Ind. Eng. Chem. Res. 1995, 34, pages 140-147
U.S. Pat. No. 4,692,423
Ivanova et al. in J. Phys. Chem. C 2007, 111, pages 4368-4374
Patcas, F. C. in Journal of Catalysis 2005, 231, pages 194-200
WO 98/29519 A1
WO 94/25151 A1
Hammon et al. in Applied Catalysis 1988, 37, pages 155-174
Li et al. in Catal. Lett. 2009, 129, pages 408-415
DD 238733 A1
McIntosh et al. in Applied Catalysis 1983, 6, p. 307-314
U.S. Pat. No. 4,049,573
Goryainova et al. in Petroleum Chemistry 2011, vol. 51, no. 3, p. 169-173
Ciambelli et al. "Acid-base catalysis in the conversion of methanol to olefins over Mg-modified ZSM-5 zeolite", Successful Design of Catalysts, Elsevier Science Publishers B.V., Amsterdam, 1988, p. 239-246
Okado et al. in Applied Catalysis 1988, 41, p. 121-135

The invention claimed is:

1. A catalyst for the conversion of oxygenates to olefins, comprising
   a honeycomb monolith support substrate including cordierite, and
   a layer applied to the monolith substrate,
   wherein the layer comprises one or more zeolites of the MFI structure type and a binder, wherein the one or more zeolites are present as a total loading of 0.08 g/cm$^3$ to 0.8 g/cm$^3$, based on the volume of the coated support substrate, and comprise Mg in a range from 2% to 7% by weight, based on the total weight of the one or more zeolites and Mg, and calculated as the metal;
   wherein the binder comprises SiO$_2$.

2. A process for preparing a catalyst according to claim 1, comprising
   (i) providing the monolith support substrate and the one or more zeolites of the MFI structure type;
   (ii) impregnating the one or more zeolites of the MFI structure type with a solution comprising Mg;
   (iii) optionally drying the one or more impregnated zeolites obtained in (ii);
   (iv) optionally calcining the one or more impregnated zeolites obtained in (ii) or (iii);
   (v) preparing a mixture comprising the one or more impregnated and optionally dried and/or calcined zeolites and one or more solvents;
   (vi) homogenizing the mixture obtained in (v) and adding a binder;
   (vii) coating the monolith support substrate with the homogenized mixture obtained in (vi);
   (viii) optionally drying the coated support substrate obtained in (vii);
   (ix) optionally calcining the coated support substrate obtained in (vii) or (viii).

3. The process according to claim 2, wherein the impregnation in step (ii) or the preparation of the mixture in step (v), or in step (vi) of the homogenizing of the mixture obtained in (v), is followed by bringing of the one or more impregnated zeolites of the MFI structure type to a particle size $D_{50}$ in the range from 0.01 to 200 µm.

4. The process according to claim 2, wherein the impregnation in step (ii) or the preparation of the mixture in step (v), or in step (vi) of the homogenizing of the mixture obtained in (v), is followed by bringing of the one or more impregnated zeolites of the MFI structure type to a particle size $D_{90}$ in the range from 0.5 to 50 μm.

5. The process according to claim 2, wherein the drying in (iii) and/or (viii) is effected at a temperature in the range from 50 to 220° C.

6. The process according to claim 2, wherein the calcining in (iv) and/or (ix) is effected at a temperature in the range from 300 to 850° C.

7. The process according to claim 2, wherein the solution used in (ii) and/or the mixture prepared in (v) comprises one or more solvents selected from the group consisting of
 a. alcohols,
 b. water,
 c. mixtures of two or more alcohols, and
 d. mixtures of water and one or more alcohols.

8. The process according to claim 2, wherein the solids concentration of the mixture prepared in (v) is in the range from 5 to 50% by weight.

9. The process according to claim 2, wherein the homogenizing in (vi) is effected by stirring, kneading, agitating, vibrating or combinations of two or more thereof.

10. The process according to claim 2, wherein the coating in (vii) is effected by spray coating and/or wash coating.

11. The process according to claim 2, wherein step (vii) is repeated once or more than once.

12. A catalyst for the conversion of oxygenates to olefins, obtained by the process according to claim 2.

13. A process for converting oxygenates to olefins, comprising
 (1) providing a gas stream comprising one or more oxygenates; and
 (2) contacting the gas stream with the catalyst according to claim 1.

14. The process according to claim 13, wherein the gas stream according to (1) comprises one or more oxygenates selected from the group consisting of aliphatic alcohols, ethers, carbonyl compounds and mixtures of two or more thereof.

15. The process according to claim 12, wherein the content of oxygenates in the gas stream according to (1) is in the range from 30 to 100% by volume based on the total volume.

16. The process according to claim 12, wherein the water content in the gas stream according to (1) is in the range from 5 to 60% by volume based on the total volume.

17. The process according to claim 12, wherein the contacting according to (2) is effected at a temperature in the range from 200 to 700° C., and a pressure in the range from 0.1 to 10 bar.

18. The process according to claim 12, wherein the process is a continuous process.

19. The process according to claim 18, in which the space velocity in the contacting according to (2) is in the range from 0.5 to 50 $h^{-1}$.

20. The process according to claim 19, in which the service life of the coated support substrate as a catalyst during which the continuous process is performed without interruption is in the range from 15 to 400 h.

21. A catalyst for the conversion of oxygenates to olefins, comprising
 a honeycomb, monolith cordierite support, and
 a layer applied to the monolith substrate, wherein the layer comprises one or more zeolites of the MFI structure type in a total loading of 0.08 to 0.2 g/cm³, based on the volume of the coated substrate, and a binder, wherein the one or more zeolites includes Mg, which is present in a range from 2 to 7% by weight, based on the total weight of the one or more zeolites of the MFI structure type and Mg, and calculated as the metal, wherein the catalyst has a relative propylene to ethylene selectivity of 78.8% to 89.3%, based on 100% by weight oxygenate conversion to propylene and ethylene;
wherein the binder comprises $SiO_2$.

22. The catalyst according to claim 21, wherein in the process for the conversion of oxygenates to olefins the catalyst has a service life of 90 to 220 hr at a space velocity in a range from 3 to 25 $hr^{-1}$.

23. The catalyst according to claim 21, wherein the catalyst has a relative propylene to butylene selectivity of 58.5% to 62%, based on 100% by weight oxygenate conversion to propylene and butylene.

* * * * *